United States Patent [19]

Igushi

[11] Patent Number: 5,682,235

[45] Date of Patent: Oct. 28, 1997

[54] DRY PARTICLE-SIZE DISTRIBUTION MEASURING APPARATUS

[75] Inventor: Tatsuo Igushi, Miyanonigashi-machi, Japan

[73] Assignee: Horiba, Ltd., Kyoto, Japan

[21] Appl. No.: 521,691

[22] Filed: Aug. 31, 1995

[30] Foreign Application Priority Data

Sep. 23, 1994 [JP] Japan .................................. 6-254410

[51] Int. Cl.$^6$ .................................................. G01N 15/02
[52] U.S. Cl. ...................... 356/335; 250/222.2; 250/577
[58] Field of Search .................................... 356/335, 336, 356/338, 73; 250/208.4, 222.2, 577

[56] References Cited

U.S. PATENT DOCUMENTS

| | | | |
|---|---|---|---|
| 4,396,911 | 8/1983 | Motsinger et al. | 250/577 |
| 5,272,354 | 12/1993 | Kosaka | 356/336 |
| 5,309,215 | 5/1994 | Schumann | 356/335 |
| 5,309,773 | 5/1994 | Tokoyama | 250/222.2 |
| 5,359,907 | 11/1994 | Baker et al. | 356/335 |

*Primary Examiner*—Richard A. Rosenberger
*Attorney, Agent, or Firm*—Poms, Smith, Lande & Rose

[57] ABSTRACT

A dry particle-size distribution measuring apparatus capable of conducting a measurement using a small quantity of sample. An optical system, a sample detector, a controller, an operating portion, and a sample-supplying portion which intermittently supplies a sample are provided. The optical system has a laser beam source emitting a laser beam, a collecting lens, and a detector which detects scattered or transmitted light. The sample supply-detecting means has a light transmitter and a light receiver provided between the sample-supplying portion and the optical system. The controlling and operating portion has a CPU which receives a detected signal from the detector and measures the particle-size distribution on the basis of the scattered or transmitted light data from the sample.

10 Claims, 3 Drawing Sheets

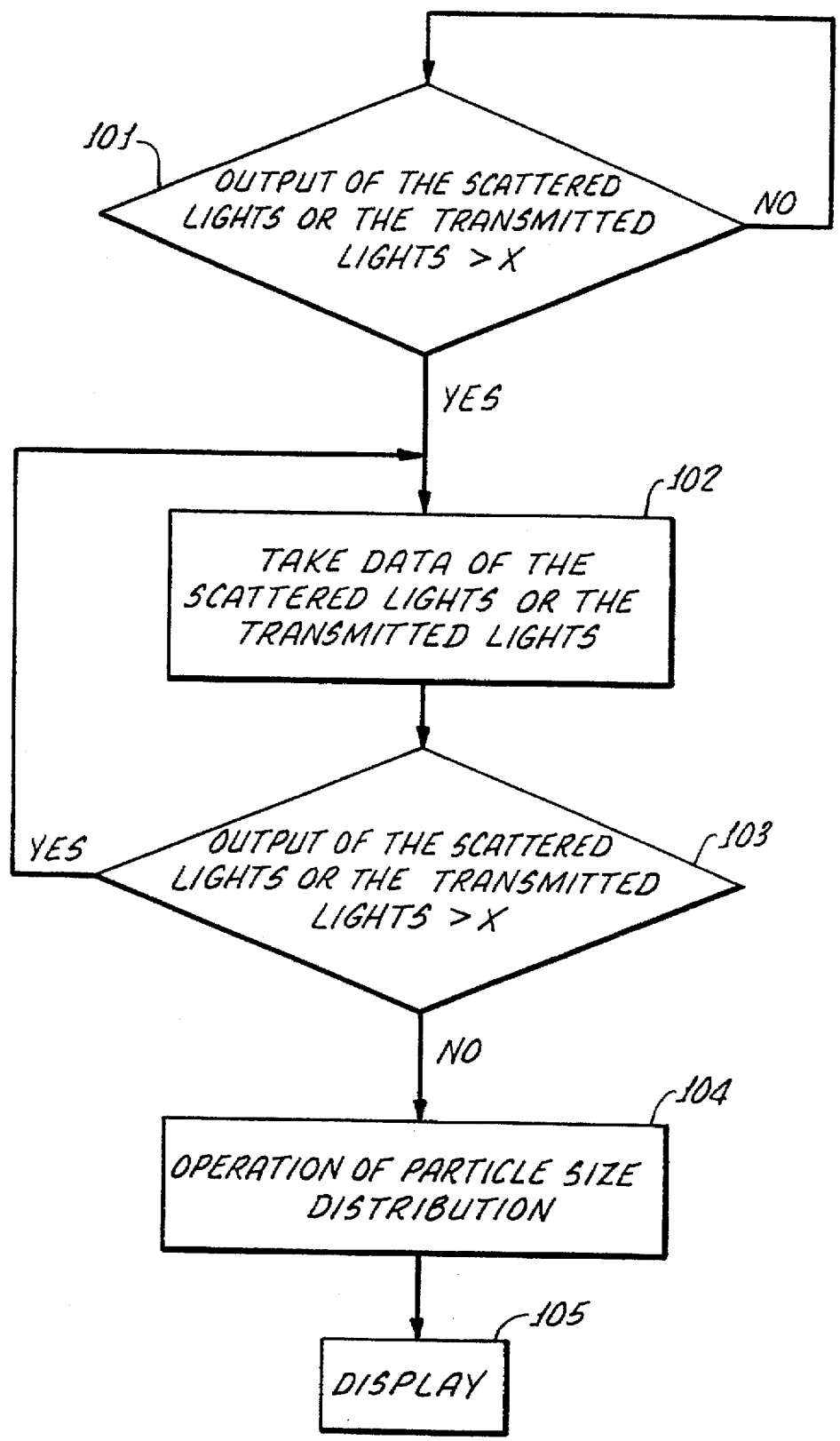

DRY PARTICLE-SIZE DISTRIBUTION MEASURING APPARATUS

BACKGROUND OF THE INVENTION

1. Field of the Invention

The present invention relates to a dry particle-size distribution measuring apparatus measuring the particle-size distribution of a powdery and particulate material.

2. Description of the Prior Art

In a dry particle-size distribution measuring apparatus measuring the particle-size of a powdery and/or particulate material (hereinafter referred to as simply a powdery and particulate material or a material), an optical system is supplied with a material sample but the sample is not circulated, so that the sample which passes through the optical system once is consumed as is.

In a conventional measurement, the optical system is first supplied with the sample, and after it has been visually confirmed that the sample has passed through the optical system, data of scattered light or transmitted light from the sample are taken. As shown in a conventional system in FIG. 4, when a sample S is supplied to an optical system 32 from a sample supplying-portion 31, after it has been visually confirmed that the sample S has passed through the optical system 32, data of scattered light or transmitted light are taken by a controlling and operating portion 34 on the basis of the detected signals from a detecting portion 33 for detecting the scattered light or transmitted light. In addition, reference numeral 35 designates a laser beam source and reference numeral 36 designates a collecting lens.

Consequently, a time lag is produced, and the portion of the sample which is not used in the measurement is consumed, so that a large quantity of sample is used in the measurement.

SUMMARY OF THE INVENTION

The present invention has been achieved in view of the above-described problems, and it is an object of the present invention to provide a dry particle-size distribution measuring apparatus capable of conducting a measurement using only a small quantity of particulate sample.

In order to achieve the above-described object, the dry particle-size distribution measuring apparatus according to the present invention, in which an optical system is supplied with a powdery and particulate sample and a particle-size distribution is measured on the basis of scattered light and/or transmitted light data from the sample, is characterized in that sample supply-detecting means detecting a sample supplied to the optical system is provided so that the scattered light or transmitted light data may be taken be a controlling and operating portion only during the time when a supply of the sample is being detected.

The sample supply-detecting means detecting the supply of the optical system with the powdery and particulate sample is provided so that the scattered light or transmitted light data may be taken in the controlling and operating portion only during the time when the supply of the sample is being detected, so that the scattered light or transmitted light data cannot be taken in until the powdery and particulate material passes through the optical system.

Consequently, it can be speedily and surely detected whether the powdery and particulate sample is passing through the optical system by means of the sample supply-detecting means, so that the powdery and particulate sample, which has not been used in the measurement, can be prevented from being consumed.

BRIEF DESCRIPTION OF THE DRAWINGS

FIG. 3 is a flow chart showing the operation of a second preferred embodiment of the present invention.

DETAILED DESCRIPTION OF THE PREFERRED EMBODIMENTS

The preferred embodiments of the present invention will be described below with reference to the drawings.

Figure 1:
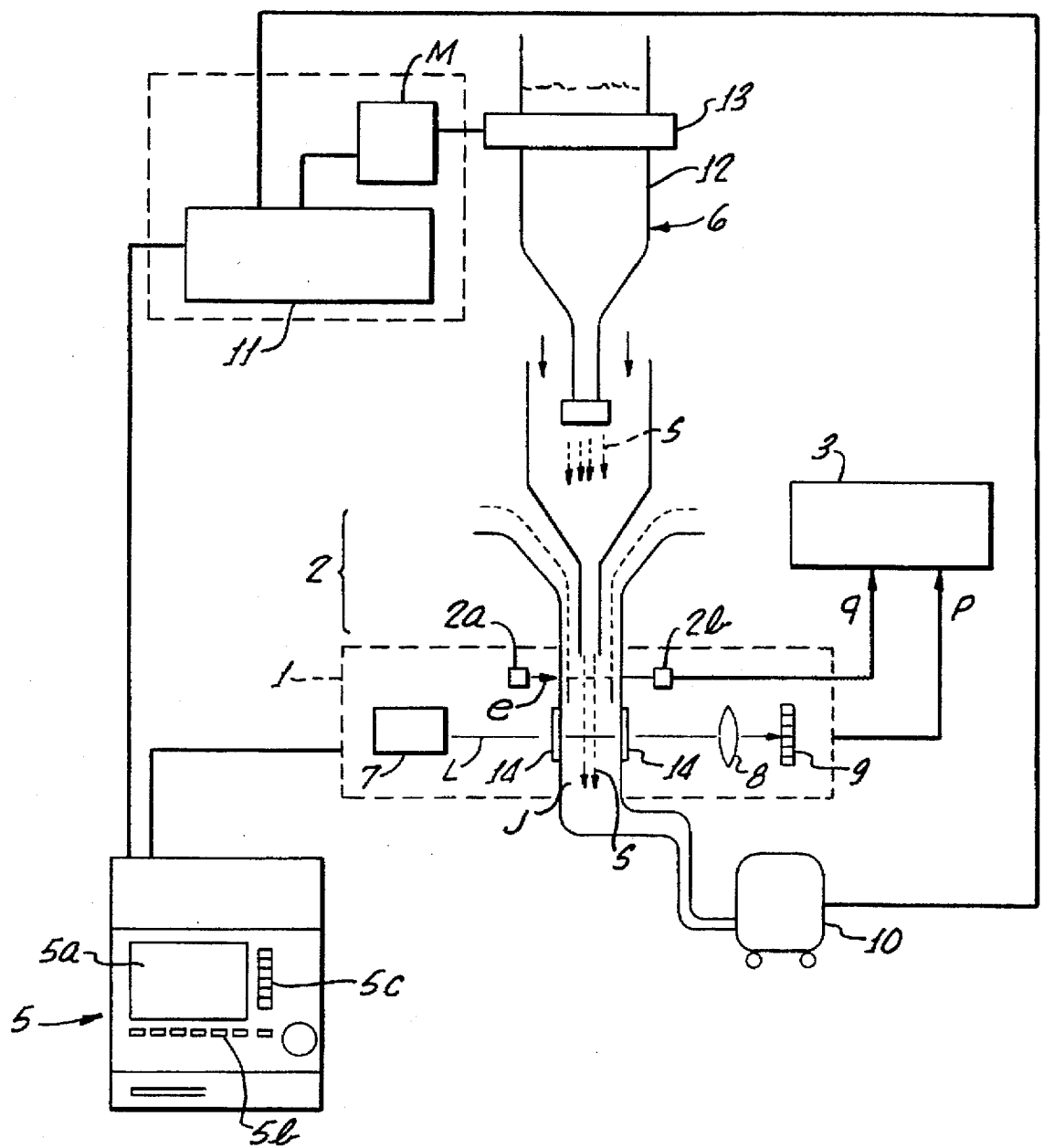
FIG. 1 is a schematic diagram showing a first preferred embodiment of the present invention.

FIG. 1 shows a first preferred embodiment of the present invention in which sample supply-detecting means for detecting whether a powdery and particulate sample has passed through an optical system or not comprises a light transmitter and a light receiver provided between a sample-supplying portion and the optical system.

Referring to FIG. 1, a dry particle-size distribution measuring apparatus generally comprises an optical system 1, sample supply-detecting means 2 or simply a sample detector, a controlling and operating portion 3 or a controller, an operating portion 5, and a sample-supplying portion of supplier 6, from which a sample S intermittently flows.

In addition, the optical system 1 further comprises a laser beam source 7 emitting a laser beam L, a collecting lens 8, and a detector 9, such as a photodiode array, for detecting scattered light or transmitted light. The sample supply-detecting means 2 comprises a light transmitter 2a and a light receiver 2b provided between the sample-supplying portion 6 and the optical system 1. The controlling and operating portion 3 comprises a CPU for receiving a detected signal p from the detector 9 and measuring a particle-size distribution on the basis of scattered light or transmitted light data from the sample taken. This particle-size distribution is displayed on a display 5a of the operating portion 5.

The supply of the sample S to the optical system 1 can be detected by crossing an output beam e emitted from the light transmitter 2a to the light receiver 2b with the sample S. A sample supply signal q is received by the CPU 3.

In operation, a suction device 10 is operated by function keys 5b, 5c of the operating portion 5 to depressurize an inside of a dry exclusive cell J from normal pressure, thereby producing a constant flow of air in the sample-supplying portion 6. Upon confirming an appointed depressurized condition within the cell J by means of a pressure sensor of a controller 11, an OK sign is displayed on the display 5a. A cup 12 with the sample S previously loaded therein is mounted on a feeder 13 and driven by an oscillating motor M, which is controlled by functions keys 5b, 5c. The sample S falls by oscillation to pass between the light transmitter 2a and the light receiver 2b, thereby entering the cell J. When the sample S passes through cell windows 14, scattered light or transmitted light from the sample S is detected by the detector 9. The particle-size distribution is calculated by the CPU 3, and the calculated particle-size distribution is displayed on the display 5a. The sample S, which has been subjected to the measurement, is then discharged from the inside of the cell J.

Figure 2:
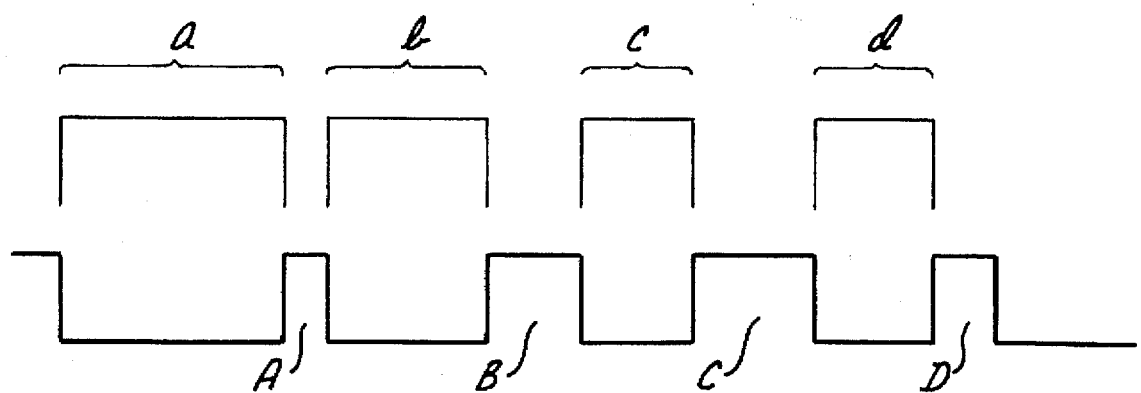
FIG. 2 is a schematic diagram illustrating a sample-supplying condition in the first preferred embodiment.
Figure 4:
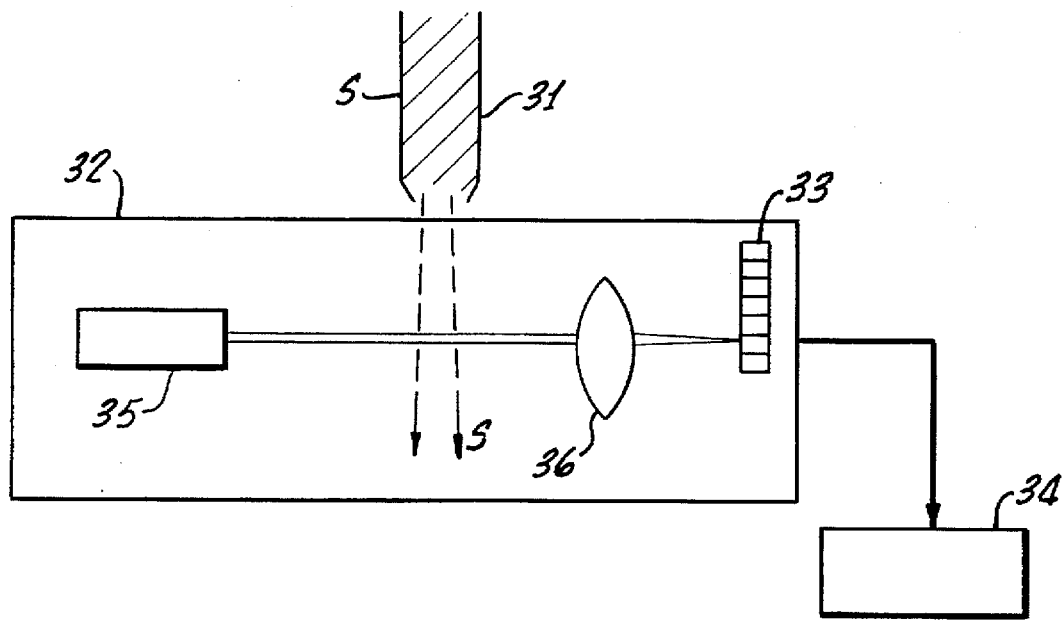
FIG. 4 is a block diagram showing the principal parts in a conventional apparatus.

According to this preferred embodiment, the output beam e is obstructed by the sample S intermittently flowing from the sample-supplying portion 6 when the sample S passes through the optical system 1. Consequently, the sample supply signal q can be detected every time the sample S flows. The sample supply signal q is output to the CPU 3, and the detected signal p from the detector 9 is output to the CPU 3; thus, data are taken which correspond to the supply of the sample S, for example, in timing intervals a, b, c, d, as shown in FIG. 2. On the other hand, when the supply of the sample S does not flow, that is during the time intervals shown by pulses A, B, C, D, the sample supply signal q is stopped, so that the CPU 3 stops taking scattered light or transmitted light data from the sample S.

As described above, according to this preferred embodiment, it can be speedily and surely detected whether the sample S passes through the optical system 1 or not by means of the sample supply-detecting means 2, so that the portion of sample S which has not been used in the measurement can be presented from being consumed, which is different from conventional apparatus. Consequently, the portion of sample S which is not used in the particle-size distribution measurement can be reduced, and thus the particle-size distribution can be measured using a small quantity of the sample S.

FIG. 3 is a flow chart showing a second preferred embodiment of the present invention in which sample supply-detecting means detecting whether a powdery and particulate sample passes through the optical system or not serves also as the detector 9 for detecting the scattered or transmitted light used in the above-described first preferred embodiment.

According to this preferred embodiment, the detector 9 detects scattered or transmitted light from the sample S intermittently flowing from the sample-supplying portion 6. When an output of the scattered or transmitted light is larger than an appointed of predetermined value X, the detected signal p is output to the CPU 3.

At first, as shown in FIG. 3, in step 101, when the sample S is supplied from the sample-supplying portion 6, the detector 9 detects that the sample S has begun to pass through the optical system 1 (i.e., the output of the scattered light or the transmitted light is greater than X), and the CPU 3 receives the scattered light or the transmitted light data by the detected signal p, as shown in step 102. Subsequently, in step 103, when the output of the scattered or the transmitted light is greater than X, the operation returns to step 102 to take scattered or transmitted light data in the CPU 3. In step 103, in the case where the output of the scattered or the transmitted light is less than X, the sample S is not supplied, and the CPU 3 does not receive any additional scattered or transmitted light data from the sample S. Thereafter, as shown by step 104, the particle-size distribution is calculated on the basis of the scattered light or the transmitted light data which have already been received by the CPU 3 in step 102. The particle-size distribution is then displayed, as shown by step 105.

Alternatively, in step 101, if the output of the scattered or the transmitted light is less than X, it can be determined that the sample S is not being supplied, and thus the operation is in stand-by mode until the sample S is supplied. Accordingly, in this preferred embodiment, it can be speedily and surely determined by the sample supply-detecting means 9 whether the sample S is passing through the optical system 1 or not, so that the portion of the sample S which is not used in the measurement of the particle-size distribution can be reduced in consumption; thus, particle-size distribution can be measured using a small quantity of the sample S.

As described above, according to the present invention, the sample supply-detecting means for detecting the supply of the optical system with the powdery and particulate sample is provided so that the scattered light or the transmitted light data may be taken by the controlling and operating portion during the time when the sample supply is being detected, so that the unused portion of the sample can be reduced in consumption; thus, particle-size distribution can be measured using only a small quantity of the sample.

What is claimed is:

1. A low sample consumption particle-size distribution measuring apparatus for measuring particle-size distribution in a small quantity of intermittently supplied particulate sample, said particle-size distribution measuring apparatus comprising:

a sample supply source for intermittently supplying a quantity of particulate sample;

a measuring cell provided with an optical system for measuring particle-size distribution in said particulate sample, said optical system including a light source for emitting light on said particulate sample, a detector for detecting scattered or transmitted light from said particulate sample, and a controller for receiving signals indicative of said detected light and for calculating particle-size distribution of said particulate sample;

a suction device for depressurizing said measuring cell so that a substantially constant flow of air is produced in said sample supply source; and a sample supply detector disposed between said sample supply source and said optical system for confirming the provision of said particulate sample to said cell.

2. The particle-size distribution measuring apparatus of claim 1 wherein said sample supply detector is a portion of said optical system.

3. A low sample consumption particle-size distribution measuring apparatus for measuring particle-size distribution in a small quantity of intermittently supplied particulate sample, said particle-size distribution measuring apparatus comprising:

a sample supply source for intermittently supplying a quantity of particulate sample;

a measuring cell including a light source;

a suction device for depressurizing said measuring cell so that a substantially constant flow of air is produced in said sample supply source;

a detector spaced from said light source for receiving light transmitted from said light source and generating a signal indicative of the level of light transmitted through said supplied particulate sample, said supplied particulate sample passable between said light source and said detector; and a controller receiving said signal from said detector when said signal is greater than or equal to a predetermined value, said controller calculating particle sized distribution of said particulate sample upon receipt of said signal.

4. The particle-size distribution measuring apparatus of claim 3 wherein said controller calculates the particle-size distribution of said supplied particulate sample based on said signal.

5. The particle-size distribution measuring apparatus of claim 3 wherein said predetermined value confirms the presence of said supplied particulate sample in said cell.

6. The particle-size distribution measuring apparatus of claim 3 further comprising a second detector generating a second signal to said controller, said second signal corresponding to said predetermined value.

7. A method for measuring the particle-size distribution of a small quantity of intermittently supplied particulate sample, said method comprising the steps of:

providing the particle-size distribution measuring apparatus of claim 3;

depressurizing said measuring cell with said suction device;

intermittently supplying a small quantity of particulate sample from said sample supply source to said measuring cell;

detecting said small quantity of particulate sample with said detector and generating said signal greater than or equal to said predetermined value indicative of the presence of said small quantity of particulate sample in said cell; and calculating the particle-size distribution based upon said signal.

8. A low sample consumption particle-size distribution measuring apparatus for measuring particle-size distribution in a small quantity of intermittently supplied particulate sample, said particle-size distribution measuring apparatus comprising:

a sample supplier for intermittently supplying a particulate sample;

a suction device for producing a substantially constant flow of air in said sample supplier;

a sample detector for detecting the presence of said particulate sample from said sample supplier and generating a sample signal indicative of the presence of said particulate sample;

an optical system having a light source for transmitting light through said particulate sample and a detector for receiving transmitted or reflected light through said particulate sample, said optical system generating a data signal indicative of the level of light received; and a controller receiving said sample signal and said data signal, said controller receiving said data signal only when said sample signal indicates the presence of said particulate sample, said controller calculating particle-size distribution of said particulate sample based upon said data signal upon receipt of said sample signal.

9. The particle-size distribution measuring apparatus of claim 8 wherein said controller calculates the particle-size distribution of said particulate sample based on said data signal.

10. The particle-size distribution measuring apparatus of claim 8 wherein said sample detector comprises a light transmitter and a light receiver disposed between said sample supplier and said optical system.

\* \* \* \* \*